United States Patent [19]

Wallach et al.

[11] Patent Number: 5,213,805
[45] Date of Patent: May 25, 1993

[54] LIPID VESICLES HAVING N, N-DIMETHYLAMIDE DERIVATIVES AS THEIR PRIMARY LIPID

[75] Inventors: Donald F. H. Wallach, Hollis; Rajiv Mathur, Nashua, both of N.H.

[73] Assignee: Micro Vesicular Systems, Inc., Nashua, N.H.

[21] Appl. No.: 735,645

[22] Filed: Jul. 25, 1991

[51] Int. Cl.$^5$ ............................................. A61K 9/127
[52] U.S. Cl. .................................... 424/450; 424/420; 428/402.2
[58] Field of Search ..................... 424/450, 405, 420; 264/4.1; 436/829; 428/402.2

[56] References Cited

U.S. PATENT DOCUMENTS

| | | | |
|---|---|---|---|
| 3,069,370 | 12/1962 | Jensen et al. | 260/23 |
| 3,372,201 | 5/1968 | Leary et al. | 260/615 |
| 3,957,971 | 5/1976 | Oleniacz | 424/70 |
| 4,075,131 | 2/1978 | Sterling | 252/542 |
| 4,182,330 | 10/1980 | Michaels | 128/260 |
| 4,217,344 | 8/1980 | Vanlerberghe et al. | 424/60 |
| 4,235,871 | 11/1980 | Papahadjopoulos et al. | 424/19 |
| 4,241,046 | 12/1980 | Papahadjopoulos | 424/19 |
| 4,247,411 | 1/1980 | Vanlerberghe et al. | 252/316 |
| 4,348,329 | 9/1982 | Chapman | 268/483 |
| 4,356,167 | 10/1982 | Kelly | 424/38 |
| 4,377,567 | 3/1983 | Geno | 424/1 |
| 4,536,324 | 8/1985 | Fujiwara | 252/311 |
| 4,544,545 | 10/1985 | Ryan et al. | 424/1.1 |
| 4,551,288 | 11/1985 | Kelly | 264/4.6 |
| 4,610,868 | 9/1986 | Fountain et al. | 424/1.1 |
| 4,666,711 | 5/1987 | Vanlerberghe et al. | 424/70 |
| 4,695,554 | 9/1987 | O'Connell et al. | 436/528 |
| 4,725,442 | 2/1988 | Haynes | 424/490 |
| 4,731,210 | 3/1988 | Weder et al. | 264/4.3 |
| 4,744,989 | 5/1988 | Payne et al. | 424/490 |
| 4,762,915 | 8/1988 | Kung et al. | 530/405 |
| 4,772,471 | 9/1988 | Vanlerberghe et al. | 424/450 |
| 4,789,633 | 12/1988 | Huang et al. | 435/240 |
| 4,832,872 | 5/1989 | Scandel | 252/547 |
| 4,855,090 | 8/1989 | Wallach | 264/4.1 |
| 4,897,308 | 1/1990 | Vanlerberghe et al. | 428/402 |
| 4,911,928 | 3/1990 | Wallach | 424/450 |
| 4,917,951 | 4/1990 | Wallach | 428/402 |
| 5,019,392 | 5/1991 | Wallach | 424/420 |
| 5,021,200 | 6/1991 | Vanlerberghe et al. | 264/4.3 |
| 5,032,457 | 7/1991 | Wallach | 428/402 |

FOREIGN PATENT DOCUMENTS

| | | |
|---|---|---|
| 0032578 | 7/1984 | European Pat. Off. |
| 0167825 | 1/1986 | European Pat. Off. |
| 59-106423 | 6/1984 | Japan |
| 61-207324 | 9/1986 | Japan |
| 8706499 | 5/1987 | PCT Int'l Appl. |
| 1539625 | 1/1979 | United Kingdom |
| 2078543 | 1/1982 | United Kingdom |
| 2079179 | 1/1982 | United Kingdom |
| 2147263 | 5/1985 | United Kingdom |
| 2166107 | 4/1986 | United Kingdom |

OTHER PUBLICATIONS

Murahami et al., J. Org. Chem. 47:2137–2144 (1982).
Gregoriadis, N. E. J. Med. 13:704–710 (1976).
Bangham et al. J. Mol. Biol. 13:238–252 (1965).
Szoha et al., Proc. Nat'l. Acad Sci. USA 75:4194–4198 (1978).
Baillie et al., J. Pharm. Pharmacol. 37:863–868 (1985).
Baille et al., J. Pharm. Pharmacol 38:502–505 (1986).
Ribier et al., Colloids and Surfaces 10:155–161 (1984).
McCuthcheon, "Detergents and Emulsifiers", No. American Edition (1973).

Primary Examiner—Thurman K. Page
Assistant Examiner—G. S. Kishore

[57] ABSTRACT

The present invention concerns lipid vesicles having dimethylamides as their primary structural lipid. Preferred dimethylamides useful in the invention are DMATO and DMASO oils. These vesicles are useful as carriers of water immiscible oily material such as fungicides. In a most preferred aspect, the invention has DMATO vesicles with TCMTB as a fungicide in trapped therein. The vesicles can be made rapidly and provide aqueous dispersion of these materials without the need for additional organic solvents.

6 Claims, No Drawings

LIPID VESICLES HAVING N, N-DIMETHYLAMIDE DERIVATIVES AS THEIR PRIMARY LIPID

REFERENCES TO RELATED APPLICATIONS

The present application is related to U. S. Pat. application Ser. No. 4,911,928, entitled "Paucilamellar Lipid Vesicles." The present application is also related to the U.S. Pat. application Ser. No. 598,120, now U.S. Pat. No. 5,160,669 entitled "Method of Making Oil Filled Paucila Lipid Vesicles." The disclosures of the aforementioned patent and patent application are incorporated herein by reference.

BACKGROUND OF THE INVENTION

The present invention concerns lipid vesicles made with materials that would not ordinarily be considered as vesicle formers. More particularly, it has been discovered that N,N-dimethylamides prepared from straight chain carboxylic acids can be formed into lipid vesicles. If the vesicles are in the form of paucilamellar lipid vesicles, these vesicles may have a water-immiscible oily material contained in their amorphous central cavity. Alternatively, the vesicles of the invention may just contain aqueous materials. The preferred materials for making these vesicles are the N,N-dimethylamides of tall oils (DMATO) or soy bean oils (DMASO).

DMATO and other N,N-dimethylamides are used as intermediates, carriers, or active ingredients in the manufacture and/or formulation of a variety of materials, including penetrants, dispersants, solvents and corrosion inhibitors. DMATO has a number of water treatment uses, particularly to control organic deposits and corrosion on surfaces. A particularly valuable use of DMATO is as a solvent or carrier for a variety of oily materials including fungicides.

One of the most important DMATO/fungicide combinations is a dispersion of 2-(thiocyanomethylthio) benzothiazole (TCMTB) in DMATO and organic solvents such as toluene. This combination is used as a fungicide in a variety of industries, including wood preservation, protection of cotton and other agricultural seedlings, and leather tanning.

However, although this combination is very effective, there are many problems associated with its agricultural and manufacturing use. The DMATO/TCMTB dispersion is not stable on its own, but rather requires an organic solvent such as toluene for stability. DMATO is insoluble in water but can be dispersed in water under certain circumstances. Oil-in-water emulsions are not the optimum way of utilizing this fungicide since it does not give an even distribution upon aerosol dispersion. In addition, the use of the organic solvents leads to solvent leaching into the environment, a pollution problem that it is difficult to control. Accordingly, a stable, aqueous dispersible TCMTB/DMATO composition which does not use organic solvents would solve many of these problems.

While lipid vesicles which encapsulate an oily material, such as those disclosed in the U. S. Pat. No. 4,911,928, are now known, the efficacy and long time approval of the DMATO/TCMTB combination makes it important to utilize this formulation. However, one would not expect to be able to make vesicles from DMATO and the other N,N-dimethylamides. Most vesicle formers are in the subclass of amphiphiles which have one end that is highly hydrophilic, e.g., polyoxyethylene or phospho groups, with the other end constituting a highly hydrophobic organic chain such as a long chain fatty acid. DMATO and the other N,N-dimethylamides do not fall within this category since they do not have this hydrophilic head group. The dimethylamides useful in the present invention all have small organic groups (i.e., methyl groups) on the amide nitrogen and only the double bonded oxygen on the neighboring carbon has a possibility of hydrogen bonding. In contrast, the diethanolamides disclosed in the aforementioned U.S. Pat. No. 4,919,928 have two ethanol ($-CH_2CH_2OH$) groups which are highly hydrophilic attached to nitrogen as well as having the double bonded oxygen. These ethanols constitute the highly hydrophilic head groups common in vesicle forming materials.

Accordingly, an object of the invention is to develop a method of delivery for a DMATO/TCMTB system which does not use organic solvents.

Another object to the invention is to provide stable lipid vesicles having N,N-dimethylamides prepared from straight chain carboxylic acids as the major lipid in the bilayer structure of the vesicles.

A further object of the invention is to produce lipid vesicles of N,N-dimethylamides of straight chain carboxylic acids having a water immiscible material encapsulated as the lipid vesicle itself.

A still further object of the invention is to provide a fungicide which is more environmentally neutral than those presently used.

These and other objects and features of the invention will be apparent for the following description and the claims.

SUMMARY OF THE INVENTION

The present invention features lipid vesicles having N,N-dimethylamides of (or prepared from) straight chain carboxylic acids as their primary bilayer-forming material. These lipid vesicles can be used to encapsulate aqueous-based materials as well as water immiscible materials. The invention further provides a method of manufacturing such lipid vesicles.

The lipid vesicles of the present invention are characterized by two or more bilayers in the form of spherical shells separated by aqueous layers. Preferably, 2–10 lipid bilayers surround an amorphous central cavity, thereby forming paucilamellar lipid vesicles. The lipid vesicles of the present invention all have N,N-dimethylamides of straight chain carboxylic acids as the primary lipid of the lipid bilayers. The term "primary lipid," as used herein, means that this lipid is the major lipid, by weight, forming the structure of the lipid bilayers The preferred N,N-dimethylamides of the present invention are prepared from straight chain carboxylic acids selected from the group consisting of $C_{12}$–$C_{18}$ chain carboxylic acids, rosin acids and mixtures thereof. These acids, which are formed into the amides, include oleic acid, linoleic, and linolenic, ricinoleic acid and mixtures thereof. Other amides particularly useful in the invention are amides of mixed carboxylic acids derived from tall oil, castor oil, corn oil, cottonseed oil, linseed oil, olive oil, peanut oil, rapeseed oil, safflower oil and soybean oil. These oils may include some small percentage of branch chain carboxylic acids.

The most preferred amides as lipid bilayer formers are DMATO (N,N-dimethylamide of tall oil) and DMASO (N,N-dimethylamide of soybean oil). These mixed oil dimethylamides form excellent vesicles and have other properties which are particularly advantageous in the present invention.

The vesicle wall or bilayer may also include a sterol such as cholesterol, hydrocortisone, or a phytosterol as well as a charge producing agent. One charge producing agent that is particularly useful, which acts not such as a charge producing but also as a structural member, is dimethyldistearylamine. The incorporation of this material into the bilayers yields a net positive charge to the vesicles.

One preferred embodiment of the invention has paucilamellar lipid vesicles with the amorphous central cavity being filled with a water immiscible oily material. This oily material may act either as a carrier for any material that is dispersible therein or may itself be an active. One example of an active is a fungicide such as 2-(thiocyanomethylthio) benzothiazole (TCMTB)

While the vesicles of the invention may be made by any methodology, those procedures set forth in the U.S. Pat. No. 4,911,928 and U. S. Pat. application No. 598,120 are preferred. Briefly, paucilamellar vesicles are made by forming a lipophilic phase of the lipid and any other lipid soluble materials, forming an aqueous phase of water and/or any aqueous soluble material to incorporate into the vesicles, and, if utilized, an oily phase is formed of any water immiscible oil materials to be incorporated. The lipid and aqueous phases (and, if desired, the oily phase) are then shear mixed to form the vesicles. The term "shear mixing" as used herein means and implies mixing such that the shear produced is the equivalent to that of a relative flow rate of 5–30m/s through a 1 mm orifice. If just the lipid phase and aqueous phase are blended together under shear mixing conditions, aqueous filled vesicles are formed. These can be used as is or gentle mixing with a water immiscible oily phase can "load" the preformed vesicles with the water immiscible material, thereby forming oil filled vesicles. Substantially equivalent oil filled vesicles can be formed at once with the three phases Further aspects of the invention will be more apparent from the following detailed description.

DETAILED DESCRIPTION OF THE INVENTION

The present invention provides methods and apparatus for forming vesicles from a variety of N,N-dimethylamides. These amides have the structure:

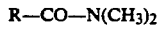

$$R-CO-N(CH_3)_2$$

where R is an alkyl chain derived from fatty acids. Fatty acids for forming the amides useful in the present invention not only include $C_{12}$-$C_{18}$ straight chain fatty acids, particularly those with one or more unsaturations, but also a broad variety of mixed fatty acids have shown particular usefulness. For example, DMATO, a preferred amide, is made from tall oil. A tall oil particularly beneficial for forming DMATO, which is then used in the present invention is a refined, low rosin content tall oil with a minimum fatty acid content of about 95% by weight. This tall oil is sold commercially under the trademark "UNITOL ACD SPECIAL" by Union Camp Corporation and has the following typical analysis:

| | |
|---|---|
| total fatty acids | 97.5% |
| rosin acids | 1.0% |
| unsaponifiables | 1.5% |
| linoleic acid | 45.1% |
| oleic acid | 49.5% |
| saturated acids | 1.6% |

DMATO oil using this tall oil is sold by Buckman Laboratories International, Inc.

DMATO based vesicles have a variety of uses, including all those for which DMATO is normally used. These include as an additive in water treatment, as a solvent cleaner, as a penetrant or as a dispersant and, particularly, as a co-solvent for agricultural pesticides and insecticides. This last use is particularly valuable since vesicular DMATO makes unnecessary the organic solvent, e. g., tolulene, that is normally needed as a co-solvent for fungicides, thereby reducing the level of toxic organic solvents in the environment which can be released by solvent leaching. This is important for DMATO/TCMTB in treatment of a variety of seeds, e.g., cotton seeds, to prevent fungal growth. This same combination is also used during tanning processes of leather for fungal protection and as a wood preservative. TCMTB, when mixed with DMATO in emulsions rather than vesicles, requires an organic solvent to stabilize the emulsion. Making a vesicle preparation eliminates the need for this organic solvent, which in turn eliminates the possibility of leaching.

The vesicles of the invention could also be used for any other classic vesicular applications. These include pharmaceuticals, cosmetics, and the industrial applications described in the literature.

The following Examples will more clearly illustrate the efficacy of the present invention.

EXAMPLE 1

In this Example, the vesicles were made using a mixture of DMATO, cholesterol and an aqueous solution of either sodium lauryl sulfate or sodium oleate. Plain water does not appear to work as well as the slightly ionic solution when an oil is not used as part of the process.

Approximately 0.9g of DMATO were mixed with 0.1g of cholesterol to form a lipophilic phase. This phase was heated to about 50° C. to dissolve the cholesterol and then was placed in a 10 ml syringe. Approximately 4ml of a 1.5% sodium lauryl sulfate solution at 45° C. was placed in another 10 ml syringe and the two syringes were connected by a three-way stopcock. The lipophilic phase and the aqueous phase were then blended through the stopcock by pushing the syringes back and forth for one to two minutes. The resulting vesicles had an aqueous uptake of about 9 ml/g of lipid. Similar results were obtained using phytosterols (Generol 122) in place of the cholesterol or using a 1.5% solution of sodium oleate in place of the 1.5% sodium lauryl sulfate solution. The formed vesicles could be loaded with mineral oil or an alkyd resin after formation to about 40% (volume/volume) uptake. Loading after formation is accomplished by taking a solution of the vesicles in one syringe, a solution of the material to be loaded in the other, and mixing gently for about a minute. This procedure is further described in the U. S. Pat. application Ser. No. 598,120.

The vesicles made using this procedure were paucilamellar lipid vesicles having a diameter of about 235 nanometers.

EXAMPLE 2

For this Example, the same materials were used as Example 1, except a water immiscible oily material, specifically TCMTB, was encapsulated within the amorphous central cavity of the lipid vesicles. One ml of DMATO was combined with 3 ml of Busan 80 (TCMTB oil—Buckman Laboratories) at 50° C. This combination was placed in a 25 ml syringe and then shear mixed with 4ml of an aqueous phase in another 25 ml syringe through a three-way stopcock using the same technique described in Example 1. The aqueous phase was a 40% glycerine solution in 1.5% sodium lauryl sulfate.

After vesicle formation, the vesicles were viewed under a microscope and centrifuged to see if there was any free TCMTB. No free oil appeared.

The vesicles are approximately 450 nanometers in diameter, or about twice the diameter of the "empty" DMATO vesicles

EXAMPLE 3

In this Example, DMATO/TCMTB vesicles, some with propylene glycol and some with external emulsified Chloroneb, another fungicide, were tested for efficacy as fungicides. The results were comparable to those obtained using normal oil-in-water emulsions except ease of application, and long term efficacy appear to be better with the vesicles.

Vesicles were manufactured using the syringe technique described in Example 2 but could also be made using a NOVAMIX ® vesicle forming apparatus from Micro Vesicular Systems, Inc., Nashua, New Hampshire. The NOVAMIX system, which was described in detail in U.S. Pat. No. 4,895,452, provides industrial scale methods which are substantially equivalent as those described in Example 2, except the NOVAMIX machine is used to provide the industrial scale shear mixing in lieu of the syringes. The DMATO/TCMTB were blended at about 50° in a 1:3 ratio at about 50° C. and vesicles were formed using an excess of an aqueous solution to form vesicles. Vesicles were separated and a concentrated TCMTB (30% a.i.) vesicle formulation was produced and diluted 1:10 with water for use in treatment of CHEMBRED DES119 cotton seed. The treated seed was either immediately planted in soil containing Pythium or Rhizoctonia, two fungi that attack cottonseed, or stored for six months. In certain formulations, a combination formulation contain the DMATO/TCMTB (9.9% a.i.) and emulsified Chloroneb (1,4-dichloro-25-dimethyoxybenzene -23.5% a.i.) were used. These formulations were tested against commercial products have substantially the same concentrations of actives.

Table 1 shows testing of seeds treated with four different formulations as well as a control. Formula 1 is a commercial TCMTB/DMATO/ Chloroneb formulation available from Wilbur-Ellis, while Formula 2 is substantially the same formulation except the DMATO/TCMTB emulsion is replaced with DMATO/TCMTB vesicles made according to the procedures described herein. Similarly, Formula 3 is a commercial DMATO/TCMTB preparation while Formula 4 is the DMATO/TCMTB vesicle formulation of the present invention. Formulas 3 and 4 do not have Chloroneb in the external phase. Formula 5 is just a water control.

The cotton seeds were treated by the formulation at the noted rate/cwt and the seeds were planted in a greenhouse until germination. Emergence of the seedlings and survival against the two different fungi is shown on Table 1.

TABLE 1

| Treatment | fl. oz/cwt | Pythium | | Rhizoctonia | |
|---|---|---|---|---|---|
| | | Percent Emergence | Percent Survival | Percent Emergence | Percent Survival |
| Formula 1 | 14.50 | 90.00 | 80.00 | 83.00 | 31.90 |
| Formula 2 | 14.50 | 94.40 | 78.80 | 81.90 | 32.50 |
| Formula 3 | 4.35 | 85.60 | 56.90 | 0.60 | 0.00 |
| Formula 4 | 3.04 | 83.80 | 32.50 | 3.80 | 0.60 |
| Water Control | 24.00 | 0.00 | 0.00 | 0.00 | 0.00 |

As expected, the formulations containing the Chloroneb show better survival against Rhizoctonia fungi then those without Chloroneb. This is because the Rhizoctonia is only slightly affected by TCMTB but is inhibited by the Chloroneb.

As can be shown from this Table, the results using the vesicles are as successful in treating the fungi as the emulsions.

Table 2 shows the results of the same experiment except the seeds were treated with the fungicide, stored for six months, and then germinated in a greenhouse. The same formulations were used.

As can be seen from Table 2, the lipid vesicle formulation provides substantially the same results as the nonvesicular commercial emulsion. This result confirms that the efficacy of the formulation is not modified by the lipid vesicle manufacturing process.

TABLE 2

| Treatment | Rate fl. oz/cwt | Pythium | | Rhizoctonia | |
|---|---|---|---|---|---|
| | | Percent Emergence | Percent Survival | Percent Emergence | Percent Survival |
| Formula 1 | 14.50 | 94.20 | 93.30 | 93.30 | 74.20 |
| Formula 2 | 14.50 | 93.30 | 93.30 | 89.20 | 66.70 |
| Formula 3 | 4.35 | 92.50 | 92.50 | 37.50 | 4.20 |
| Formula 4 | 3.04 | 94.20 | 94.20 | 47.50 | 6.70 |
| Water Control | 24.00 | 86.70 | 86.70 | 27.50 | 1.70 |

Table 3 shows a substantially similar experiment to that shown in Table 1 except three different formulations of the TCMTB/DMATO vesicles of the inventions were used. Formula 2 is the same emulsion as shown in Table 1, TCMTB/DMATO vesicles in the Chloroneb, while Formula 4 is the TCMTB/DMATO vesicles without the external Chloroneb. Formula 6, which is a new formulation not shown on Table 1, is the TCMTB/DMATO formula with 20% propylene glycol in As can be seen from Table 3, the formulations using the lipid vesicles are just as efficacious as the formulations without the lipid vesicles.

TABLE 3

| Treatment | Rate fl. oz/cwt | Pythium | | Rhizoctonia | |
|---|---|---|---|---|---|
| | | Percent Emergence | Percent Survival | Percent Emergence | Percent Survival |
| Formula 1 | 14.50 | 97.50 | 97.50 | 96.70 | 94.50 |
| Formula 2 | 11.45 | 94.20 | 93.30 | 97.50 | 95.00 |

TABLE 3-continued

| Treatment | Rate fl. oz/cwt | Pythium | | Rhizoctonia | |
| --- | --- | --- | --- | --- | --- |
| | | Percent Emergence | Percent Survival | Percent Emergence | Percent Survival |
| Formula 3 | 4.35 | 95.00 | 95.00 | 89.20 | 41.70 |
| Formula 4 | 3.56 | 94.20 | 94.20 | 90.00 | 60.80 |
| Formula 6 | 04.98 | 93.30 | 93.30 | 90.80 | 54.20 |
| Untreated (Control) | — | 93.30 | 93.30 | 76.70 | 27.50 |

EXAMPLE 4

In this Example, DMASO (N,N-dimethylamide of soybean oil) was used in place of the DMATO oil. DMASO vesicles were made using 2 ml DMASO and 8 ml of 1.5% SLS solution in water. The phases were mixed at room temperature using the syringe technique of Example 1, forming vesicles. Similarly, vesicles were made using 1.45 ml DMASO, 2.56 ml TCMTB and 5.99 ml 20% propylene glycol in 1.5% SLS at room temperature. Other high temperature materials such as alkyds could also be incorporated into the vesicles at elevated temperatures.

The foregoing examples and description are illustrative only and those skilled in the art may find that the materials and methods will accomplish the same results. Such other materials and methods include the following claims.

What is claimed is:

1. Paucilamellar lipid vesicles characterized by about two to ten lipid bilayers in the form of spherical shells separated by an aqueous solution, said lipid vesicles having as their primary lipids in the bilayers N,N-dimethylamides of the fatty acids present in oils selected from the group consisting of tall oil and soybean oil.

2. The lipid vesicles of claim 1 wherein said lipid bilayers further comprise a sterol selected from the group consisting of cholesterol, hydrocortisone, phytosterols, and mixtures thereof.

3. The lipid vesicles of claim 1 wherein said lipid bilayers further comprise a charge producing agent selected from the group consisting of dimethyldistearyl amine, dicetyl phosphate, cetyl sulphate, phosphatidic acid, phosphatidyl serine, retinoic acid, oleic acid, palmitic acid, stearylamines, oleylamines, and mixtures thereof.

4. The lipid vesicles of claim 1 wherein said tall oil comprises no more than 5 percent rosin acids by weight.

5. The lipid vesicles of claim 1, having an inner lipid bilayer forming a central cavity, the central cavity containing a water immiscible fungicide.

6. The lipid vesicles of claim 5, wherein said fungicide is a 2-(thiocyanomethyl) benzothiazole.

* * * * *